(12) United States Patent
Otte et al.

(10) Patent No.: US 7,968,700 B2
(45) Date of Patent: Jun. 28, 2011

(54) EXPRESSION AUGMENTING DNA FRAGMENTS, USE THEREOF, AND METHODS FOR FINDING THEREOF

(75) Inventors: Arie Pieter Otte, Amersfoort (NL); Henricus Johannes Maria Van Blokland, Wijdewormer (NL); Theodorus Hendrikus Jacobus Kwaks, Amsterdam (NL); Richard George Antonius Bernardus Sewalt, Arnhem (NL)

(73) Assignee: Chromagenics B.V., Leiden (NL)

( * ) Notice: Subject to any disclaimer, the term of this patent is extended or adjusted under 35 U.S.C. 154(b) by 215 days.

(21) Appl. No.: 12/225,355

(22) PCT Filed: Mar. 20, 2007

(86) PCT No.: PCT/EP2007/052664
§ 371 (c)(1),
(2), (4) Date: Sep. 19, 2008

(87) PCT Pub. No.: WO2007/107578
PCT Pub. Date: Sep. 27, 2007

(65) Prior Publication Data
US 2010/0190207 A1    Jul. 29, 2010

Related U.S. Application Data

(60) Provisional application No. 60/784,133, filed on Mar. 20, 2006.

(30) Foreign Application Priority Data

Mar. 20, 2006   (EP) ..................................... 06111381

(51) Int. Cl.
*C07H 21/04* (2006.01)
*C12N 15/85* (2006.01)
(52) U.S. Cl. ....................... 536/24.1; 435/325
(58) Field of Classification Search ........................ None
See application file for complete search history.

(56) References Cited

U.S. PATENT DOCUMENTS

| 5,122,458 A | 6/1992 | Post et al. |
| 5,561,053 A | 10/1996 | Crowley |
| 5,994,128 A | 11/1999 | Fallaux et al. |
| 2006/0141577 A1 | 6/2006 | Otte et al. |

FOREIGN PATENT DOCUMENTS

| EP | 1 273 666 | 1/2003 |
| WO | WO 94/23046 | 10/1994 |
| WO | WO 96/04390 | 2/1996 |
| WO | WO 00/05393 | 2/2000 |
| WO | WO 00/09749 | 2/2000 |
| WO | WO 00/63403 | 10/2000 |
| WO | WO 01/02553 | 1/2001 |
| WO | WO 02/24930 | 3/2002 |
| WO | WO 02/074969 | 9/2002 |
| WO | WO 02/099070 | 12/2002 |
| WO | WO 02/099089 | 12/2002 |
| WO | WO 03/004704 | 1/2003 |
| WO | WO 2004/027072 | 4/2004 |
| WO | WO 2005/040377 | 5/2005 |
| WO | WO 2006/048459 | 5/2006 |
| WO | WO 2007/096399 | 8/2007 |

OTHER PUBLICATIONS

AC069285, Oct. 8, 2003.*
PCT International Search Report for Application PCT/EP2007/052664, dated May 25, 2007, 4 pages.
PCT Written Opinion of the International Searching Authority for Application PCT/EP2007/052664, dated May 25, 2007, 5 pages.
Homo sapiens BAC clone RP11-196D18 from 7, complete sequence, Database EMBL, May 26, 2000, accession No. AC069285.
Pantroglodytes BAC clone RP43-2A11 from 7, complete sequence, Database EMBL, Aug. 2, 2003, accession No. AC146157.
Human DNA sequence from clone RP11-407P15 on chromosome 9, Database EMBL, Aug. 9, 2002, accession No. AL845331.
Human DNA sequence from clone RP11-250K24 on chromosome 9 Contains a calponin 2 (CNN2) pseudogene and a novel pseudogene, Jun. 19, 2002, accession No. AL773524.

* cited by examiner

*Primary Examiner* — Celine Qian
(74) *Attorney, Agent, or Firm* — TraskBritt, P.C.

(57) ABSTRACT

The invention provides recombinant DNA molecules comprising novel expression augmenting DNA fragments and an expression cassette, said expression cassette comprising a heterologous promoter linked to a nucleic acid of interest. The invention further provides uses of the novel expression augmenting DNA fragments. The invention further provides methods for obtaining novel expression augmenting DNA fragments.

8 Claims, 2 Drawing Sheets

SEQUENCE LISTING

<160> NUMBER OF SEQ ID NOS: 4

<210> SEQ ID NO 1
<211> LENGTH: 38
<212> TYPE: DNA
<213> ORGANISM: Artificial
<220> FEATURE:
<223> OTHER INFORMATION: primer A (for obtaining expression augmenting
      DNA fragments from screen)

<400> SEQUENCE: 1
gatcggcgcg cccgaaaggg cccgtacctt aattaaag                               38

<210> SEQ ID NO 2
<211> LENGTH: 39
<212> TYPE: DNA
<213> ORGANISM: Artificial
<220> FEATURE:
<223> OTHER INFORMATION: primer B (for obtaining expression augmenting
      DNA fragments from screen)

<400> SEQUENCE: 2
aggcggcgcg cccgcgaaat taggcaaagg aattatcag                              39

<210> SEQ ID NO 3
<211> LENGTH: 656
<212> TYPE: DNA
<213> ORGANISM: Homo sapiens
<220> FEATURE:
<221> NAME/KEY: expression augmenting DNA fragment 47D
<222> LOCATION: (1)..(656)

<400> SEQUENCE: 3
gatctaatga tgaaaataga caaagtggca ggatggaaaa agacactcca tgcaaatgtt       60
aaccaaacga gaggtggaga gctaattata ttaagtcaaa agctgtcata ttttataaaa      120
tatagtttaa gtcaaaactc acaagagaca acaaggaca ttatagtata ataaaatggt       180
tcattcactg gaaccctatt tatatctgct accagggttc ccaaatattt aaagcaagca      240
ttgacagaaa tgaatataac aatgggagag tacttcaata ctttcagtaa tgaataataa      300
agcatgacag aacattaata agggaacaaa gaacttgaaa gcagtgtaaa gcaattacac      360
ctaaaagacg tatacaggac acaccacaca acagcagaat ccacaaactt ttcgaaagct      420
cataagaaaa ttctcctgga tacaacacct tttatctcac aagacaagtc ttaatccatg      480
tttaaactgg aatcttacgc attattattt ttggccaaat tgtgtgaaac taaaaatcac      540
taacaacagg aaaacaaaaa aaacacaaaa tatgaaaatt aaacaataca ctcttaagca      600
tgctcttgtt caaaggttgg aagactgtga agatggccat actgaccaaa ttgatc         656

<210> SEQ ID NO 4
<211> LENGTH: 729
<212> TYPE: DNA
<213> ORGANISM: Homo sapiens
<220> FEATURE:
<221> NAME/KEY: expression augmenting DNA fragment 44F
<222> LOCATION: (1)..(729)

<400> SEQUENCE: 4
gatccctaat gctgacccaa ttaaatttgt ggttttggca tagcaaggtt tattgattga       60
tcaatgctgt gtgtatggtg gatatgcttg ccttgtctca cagaaaggca acaagcagc      120 ccattatatt aaagcatgtg gattacgttt tagtccctat ggaaaaataa tataacttcc      180

```
ttgttcttac tccaatcttt aaggatctca aataagagaa aaataattgc ataattcatc      240
gtcttttgtg atttgagaca tacatgatca tgttattggc agaaaatgaa ttggttttat      300
acattttgtt gataagtgtt cccaaacatt tgtaattagt tgaccatatt cttgtttctc      360
caccttcaga agaactggtt attatgattg cttttagga aggtggtaat tacaaaatag       420
aaatgagctg aatgaaatta aagagaaact gaaaaaagaa attccttgcg aggaaataat      480
ttcatttgaa cgagtacaaa gttctttgca attcttgctt agctgaagtg tatttctagt      540
tgtgtttcca gatttatatc attatgaaaa tagccacttc ctaggttctc atttttcata      600
tacaatgttc actaggaata aatttcttcc ctggattcaa tttctgaata ttcacaaggt      660
gaaaattgtg ttcacctctt ttcagatgga gattctctga actgtaattg ggtgactatt      720
tcatagatc                                                              729
```

EXPRESSION AUGMENTING DNA FRAGMENTS, USE THEREOF, AND METHODS FOR FINDING THEREOF

CROSS-REFERENCE TO RELATED APPLICATION

This application is the national phase entry of PCT International Application No. PCT/EP2007/052644, filed on Mar. 20, 2007, designating the United States of America, and published, in English, as PCT International Publication No. WO 2007/107578 A1 on Sep. 27, 2007, which PCT International Application claims priority from U.S. Ser. No. 60/784,133 filed on Mar. 20, 2006 and from EP 06111381.7 filed on Mar. 20, 2006. This patent application also claims priority under 35 U.S.C. §119(e) to U.S. Ser. No. 60/784,133 filed on Mar. 20, 2006.

The invention relates to the field of molecular biology and biotechnology. More specifically the present invention relates to means and methods for improving recombinant DNA expression.

Proteins can be produced in various host cells for a wide range of applications in biology and biotechnology, for instance as biopharmaceuticals. Eukaryotic and particularly mammalian host cells are preferred for this purpose for expression of many proteins, for instance when such proteins have certain posttranslational modifications such as glycosylation. Methods for such production are well established, and generally entail the expression in a host cell of a nucleic acid (also referred to as 'transgene') encoding the protein of interest. In general, the transgene together with a selectable marker gene is introduced into a precursor cell, cells are selected for the expression of the selectable marker gene, and one or more clones that express the protein of interest at high levels are identified, and used for the expression of the protein of interest.

DNA elements that in general improve expression of recombinant DNA in eukaryotic cells have been described. Examples of such elements are anti-repressor elements, such as STAR elements (WO 03/004704; Kwaks et al, 2003), Matrix Attachment Regions (MAR) (e.g. Phi-Van et al, 1990; WO 02/074969, WO 2005/040377), insulator elements (e.g. West et al, 2002; Chung et al, 1993, 1997; Kellum and Schedl, 1991; WO 94/23046, WO 96/04390, WO 01/02553, WO 2004/027072), UCOE (WO 00/05393, WO 02/24930, WO 02/099089, WO 02/099070). These elements may at least in part function by counteracting the repressive effects of chromatin.

Another example of elements that improves recombinant expression are so-called Expression Augmenting Sequence Elements (EASE) as described in EP 0873405 B1. Such elements were obtained from Chinese hamster ovary (CHO) cell genomic DNA.

Several of the described DNA elements that improve expression have a considerable length, often being longer than 1 kb and sometimes being several kb in length, which makes them in some instances less easy to manipulate and clone in the desired configuration in for instance expression plasmids.

In addition, different types of elements might act differently and hence there may be potential to improve recombinant expression by intervening at different molecular levels.

There remains a need in the art to improve expression of recombinant DNA in mammalian cells. The present invention aims at providing means and methods for this purpose.

SUMMARY OF THE INVENTION

A novel concept for selecting host cells expressing high levels of polypeptides of interest was disclosed in international application PCT/EP2005/055794 (published as WO 2006/048459), which was filed before but published after the priority date of the instant application. An alternative was disclosed in U.S. patent application Ser. No. 11/359,953 (published as US 2006/0141577) and in international application PCT/EP2007/051696, also filed before but published after the priority date of the instant application. The disclosures of applications PCT/EP2005/055794, U.S. Ser. No. 11/359,953 and PCT/EP2007/051696 are incorporated in their entirety by reference herein. Briefly, those applications teach the use of a sequence encoding a selectable marker polypeptide with a non-ATG startcodon, e.g. a GTG or TTG. This resulted in the possibility to select clones with high stringency and was used to obtain clones of host cells with very high expression levels.

The present invention exploits the selection stringency obtained by such sequences encoding a selectable marker polypeptide with a GTG or TTG startcodon, for a novel screen capable of obtaining expression augmenting DNA fragments. Methods to screen for anti-repressor elements have been described in the prior art, e.g. in WO 00/09749, but in contrast to the present methods such methods used DNA encoding selectable marker proteins having a normal startcodon, i.e. an ATG startcodon.

In one aspect the present invention provides a method of obtaining an expression augmenting DNA fragment, which method comprises the steps of: 1) providing a a variety of fragment-comprising vectors, said vectors comprising DNA fragments having a size of between about 50 and 5000 base pairs, said DNA fragments being located at a distance of less than about 5000 base pairs from a transcription unit, said transcription unit comprising a promoter operably linked to sequence encoding a selectable marker protein that protects a host cell from the lethal or growth-inhibitory effects of a selection agent, wherein the sequence encoding the selectable marker protein has a GTG startcodon or a TTG startcodon; 2) introducing the fragment-comprising vectors into host cells; 3) culturing the host cells in the presence of the selection agent; and 4) obtaining the expression augmenting DNA fragment from host cells that still can grow in the presence of the selection agent after at least two weeks.

The invention further provides a library comprising a variety of fragment-comprising vectors, said vectors comprising DNA fragments having a size of between about 50 and 5000 base pairs, said DNA fragments being located at a distance of less than about 5000 base pairs from a transcription unit, said transcription unit comprising a promoter operably linked to sequence encoding a selectable marker protein that protects a host cell from the lethal or growth-inhibitory effects of a selection agent, wherein the sequence encoding the selectable marker protein has a GTG startcodon or a TTG startcodon.

The invention further provides the use of an expression augmenting DNA fragment obtained by a method of the invention, for increasing the expression level from an expression cassette in a DNA molecule.

In another aspect, the invention further provides a recombinant DNA molecule comprising an expression augmenting DNA fragment selected from the group consisting of: a) SEQ. ID. NO. 3 (47D); b) SEQ. ID. NO. 4 (44F); c) fragments of a) or b), wherein said fragment has expression augmenting activity; and d) sequences that are at least 70% identical in nucleotide sequence to a), b) or c), wherein said sequences have expression augmenting activity; said recombinant DNA molecule further comprising an expression cassette, said expression cassette comprising a heterologous promoter linked to a nucleic acid of interest.

The invention also provides a cell comprising a recombinant DNA molecule according to the invention.

The invention further provides a method for producing a protein of interest, comprising culturing a cell comprising a recombinant DNA molecule according to the invention to express the nucleic acid encoding the protein of interest in said cell.

DETAILED DESCRIPTION OF THE INVENTION

Figure 1:
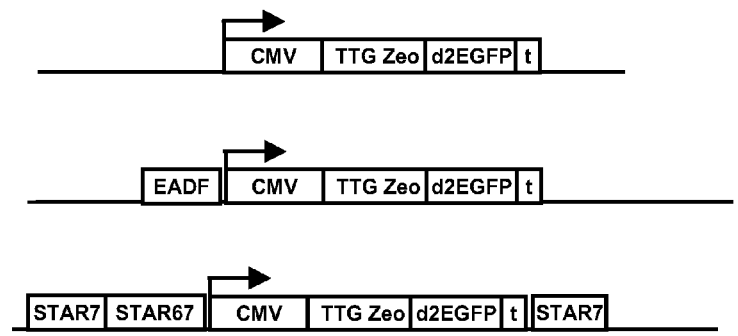
FIG. 1. Results with expression augmenting DNA fragments (EADF) 44F and 47D in expression constructs, in CHO-K1 cells. The control expression construct does not contain EADF or STAR sequences. As another control, expression of a construct with STAR7 flanking the construct and STAR67 upstream of the promoter is shown. See example 1 for details. Dots indicate individual data points; lines indicate the average expression levels; used constructs are indicated on the horizontal axis, and schematically depicted above the graph; vertical axis indicates d2EGFP signal in zeocin-resistant clones.
Figure 1:
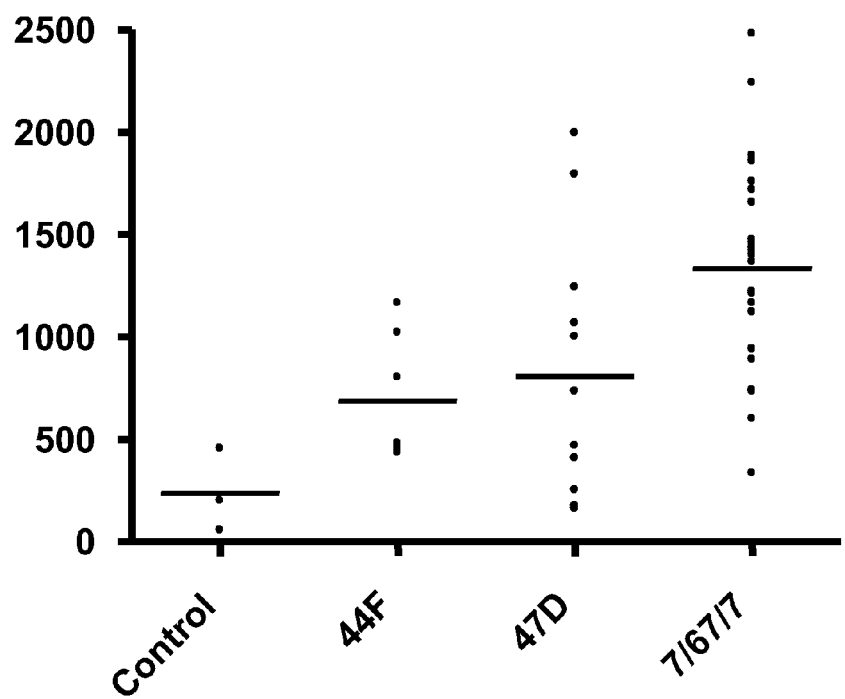

The term "monocistronic gene" is defined as a gene capable of providing a RNA molecule that encodes one polypeptide. A "multicistronic transcription unit", also referred to as multicistronic gene, is defined as a gene capable of providing an RNA molecule that encodes at least two polypeptides. The term "bicistronic gene" is defined as a gene capable of providing a RNA molecule that encodes two polypeptides. A bicistronic gene is therefore encompassed within the definition of a multicistronic gene.

A "polypeptide" as used herein comprises at least five amino acids linked by peptide bonds, and can for instance be a protein or a part, such as a subunit, thereof. Mostly, the terms polypeptide and protein are used interchangeably herein.

A "gene" or a "transcription unit" as used in the present invention can comprise chromosomal DNA, cDNA, artificial DNA, combinations thereof, and the like. Transcription units comprising several cistrons are transcribed as a single mRNA.

DNA molecules of the invention can be present in the form of double stranded DNA, having with respect to the selectable marker polypeptide and/or the polypeptide of interest a coding strand and a non-coding strand, the coding strand being the strand with the same sequence as the translated RNA, except for the presence of T instead of U. Hence, an AUG startcodon is coded for in the coding strand by an ATG sequence, and the strand containing this ATG sequence corresponding to the AUG startcodon in the RNA is referred to as the coding strand of the DNA. It will be clear that startcodons or translation initiation sequences are in fact present in an RNA molecule, but that these can be considered equally embodied in a DNA molecule coding for such an RNA molecule; hence, wherever the present invention refers to a startcodon or translation initiation sequence, the corresponding DNA molecule having the same sequence as the RNA sequence but for the presence of a T instead of a U in the coding strand of said DNA molecule is meant to be included, and vice versa, except where explicitly specified otherwise. In other words, a startcodon is for instance an AUG sequence in RNA, but the corresponding ATG sequence in the coding strand of the DNA is referred to as startcodon as well in the present invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

A translation start sequence is often referred to in the field as 'Kozak sequence', and an optimal Kozak sequence is RCC ATGG, the startcodon underlined, R being a purine, i.e. A or G (see Kozak M, 1986, 1987, 1989, 1990, 1997, 2002). Hence, besides the startcodon itself, the context thereof, in particular nucleotides −3 to −1 and +4, are relevant, and an optimal translation startsequence comprises an optimal startcodon (i.e. ATG) in an optimal context (i.e. the ATG directly preceded by RCC and directly followed by G). Translation by the ribosomes starts preferably at the first startcodon it encounters when scanning from the 5'-cap of the mRNA (scanning mechanism), and is most efficient when an optimal Kozak sequence is present (see Kozak M, 1986, 1987, 1989, 1990, 1997, 2002). However, in a small percentage of events, non-optimal translation initiation sequences are recognized and used by the ribosome to start translation. The invention makes use of this principle, and allows for decreasing the amount of translation and hence expression of the selectable marker polypeptide, which can therefore be used to increase the stringency of the selection system, and thereby new expression augmenting DNA fragments can be identified. To this purpose, the ATG startcodon itself of the selectable marker polypeptide is mutated into a GTG startcodon or into a TTG startcodon.

The coding sequences of the selectable marker protein of WO 2006/048459 and US 2006/0141577 in preferred embodiments have a GTG or more preferably a TTG startcodon. As a consequence of the stringent selection system with a GTG or TTG startcodon for the selectable marker coding sequence, no or almost no clones will evolve, unless the vector has incorporated an expression augmenting DNA fragment. Therefore, this system allows the detection and isolation of such novel elements with high stringency and high efficiency.

In one aspect, the present invention therefore provides a method of obtaining an expression augmenting DNA fragment, which method comprises the steps of: 1) providing a a variety of fragment-comprising vectors, said vectors comprising DNA fragments having a size of between about 50 and 5000 base pairs, said DNA fragments being located at a distance of less than about 5000 base pairs from a transcription unit, said transcription unit comprising a promoter operably linked to sequence encoding a selectable marker protein that protects a host cell from the lethal or growth-inhibitory effects of a selection agent, wherein the sequence encoding the selectable marker protein has a GTG startcodon or a TTG startcodon; 2) introducing the fragment-comprising vectors into host cells; 3) culturing the host cells in the presence of the selection agent; and 4) obtaining the expression augmenting DNA fragment from host cells that still can grow in the presence of the selection agent after at least two weeks. This aspect of the invention is referred to as the screening method of the invention.

The DNA fragments can for instance be suitably obtained from the genome of a cell, including a mammalian cell, for instance from a human cell, a mouse cell, a hamster cell, a rat cell, and the like. The fragments can for instance also be obtained from a library of a part of or a complete genome. Genomes of other organisms could also be used as the source for the DNA fragments, including for instance plants, yeast, *C. elegans*, zebrafish, *Drosophila*, etc, or even of bacteria or viruses. In principle, synthetic DNA fragments could also be tested in the screening method of the invention. The fragments can be cloned by conventional molecular biology techniques into the vectors, thus obtaining the variety of fragment-containing vectors. In preferred embodiments, the fragments have a size of between about 100 and 2000 base pairs, more preferably between about 200 and 1000 base pairs. The advantage of using fragments with an average smaller size is that expression augmenting DNA fragments that will be selected will be smaller and thus easier to manipulate because they will provide less burden on the capacity, i.e. the available space for cloning DNA of interest, of expression vectors in which they will be used.

In certain embodiments, the DNA fragments are located upstream of the promoter of the transcription unit. It is also possible to screen with vectors wherein the fragments are in different locations, for instance downstream of the transcription unit. In preferred embodiments, the fragments are located at a distance of less than about 2000 base pairs from the transcription unit. Lowering the distance between the fragments and the transcription unit prevents that certain fragments would have expression augmenting activity but would go undetected because they might work better when placed closer to the transcription unit. In more preferred embodiments, the DNA fragments are located at a distance of less than 800, 700, 600, preferably less than about 500, 400, 300, 200, 100 or 50 base pairs from the transcription unit. In certain embodiments, the fragments are located upstream of the promoter of the transcription unit and the end of the fragments are separated by less than 500, preferably less than 200, more preferably less than 100 or less than 50 base pairs from the start of the promoter sequence.

The selection agent may be any selection agent that confers lethal or growth-inhibitory effects to host cells, and the examples for selection agents described in WO 2006/048459 can for instance be used. In a preferred embodiment, the selection agent is zeocin. It has been disclosed in WO 2006/048459 that sequences encoding a selectable marker protein providing resistance to a selection agent with a GTG or a TTG startcodon do function in stringent selection methods. It is clear therefrom that a wide variety of possibilities regarding selectable marker proteins exist and are functional, and thus could in principle be employed in the screening method of the present invention to find expression augmenting DNA fragments. In a preferred embodiment, the sequence encoding the selectable marker has a TTG startcodon.

The term "selection marker" or "selectable marker" is typically used to refer to a gene and/or protein whose presence can be detected directly or indirectly in a cell, for example a polypeptide that inactivates a selection agent and protects the host cell from the agent's lethal or growth-inhibitory effects (e.g. an antibiotic resistance gene and/or protein). Another possibility is that said selection marker induces fluorescence or a color deposit (e.g. green fluorescent protein (GFP) and derivatives (e.g d2EGFP), luciferase, lacZ, alkaline phosphatase, etc.), which can be used for selecting cells expressing the polypeptide inducing the color deposit, e.g. using a fluorescence activated cell sorter (FACS) for selecting cells that express GFP. Selectable marker polypeptides are well known in the art and routinely used when eukaryotic host cell clones are to be obtained, and several examples of suitable selectable marker proteins are provided in WO 2006/048459. DNA sequences coding for such selectable marker polypeptides are known, and several examples of wild-type sequences of DNA encoding selectable marker proteins are provided in WO 2006/048459 (e.g. FIGS. 15-21 therein, incorporated by reference herein). It will be clear that mutants or derivatives of selectable markers can also be suitably used, and are therefore included within the scope of the term 'selectable marker polypeptide', as long as the selectable marker protein is still functional. A selectable marker polypeptide according to the invention is a protein that is encoded by nucleic acid, which polypeptide can be functionally used for selection, for instance because it provides resistance to a selection agent such as an antibiotic. Hence, when an antibiotic is used as a selection agent, the DNA encodes a polypeptide that confers resistance to the selection agent, which polypeptide is the selectable marker polypeptide. In certain embodiments, a selection marker used for the invention is zeocin. The person skilled in the art will know that other selection markers are available and can be used, e.g. blasticidin, neomycin, puromycin, bleomycin, hygromycin, etc. In other embodiments, kanamycin is used. In yet other embodiments, the DHFR gene is used as a selectable marker, which can be selected for by methotrexate, especially by increasing the concentration of methotrexate cells can be selected for increased copy numbers of the DHFR gene (or alternatively, the DHFR gene can be selected for in the absence of methotrexate in cells that are dhfr-deficient). Similarly, the glutamine synthetase (GS) gene can be used, for which selection is possible in cells having insufficient GS (e.g. NS-0 cells) by culturing in media without glutamine, or alternatively in cells having sufficient GS (e.g. CHO cells) by adding an inhibitor of GS, methionine sulphoximine (MSX). Other selectable marker genes that could be used, and their selection agents, are for instance described in table 1 of U.S. Pat. No. 5,561,053; see also Kaufman, Methods in Enzymology, 185:537-566 (1990), for a review of these. It will be clear that a 'selection marker protein that protects a host cell from the lethal or growth-inhibitory effects of a selection agent' can also include proteins that protect the cells from dying in the absence of a compound that is required for growth (i.e. the selection agent can in certain embodiments be a culture medium lacking one or more compounds required for growth). The term "selection" is typically defined as the process of using a selection marker/selectable marker and a selection agent to identify host cells with specific genetic properties (e.g. that the host cell contains a transgene integrated into its genome). For convenience and as generally accepted by the skilled person, in many publications as well as herein, often the gene and protein encoding the resistance to a selection agent is referred to as the 'selectable agent (resistance) gene' or 'selection agent (resistance) protein', respectively, although the official names may be different, e.g. the gene coding for the protein conferring resistance to neomycin (as well as to G418 and kanamycin) is often referred to as neomycin (resistance) (or neo$^r$) gene, while the official name is aminoglycoside 3'-phosphotransferase gene.

In principle, the use of one selectable marker protein suffices for obtaining expression augmenting DNA fragments, since the screening method of the present invention is primarily aimed at identifying a suitable expression augmenting DNA fragment. In contrast, the methods disclosed in WO 2006/048459 and US 2006/0141577 were aimed at providing selection conditions to obtain cells with high expression of a polypeptide of interest. Hence, the difference is that for the present screening method, a polypeptide of interest does not necessarily play a role. Therefore, the transcription unit may in some embodiments be a monocistronic transcription unit, which will then only encode the selectable marker protein.

However, in certain embodiments, the transcription unit is a multicistronic transcription unit, such as a bicistronic transcription unit, which comprises the sequence encoding the selectable marker protein that provides resistance to a growth inhibitor, and further comprises a sequence encoding a protein of which the presence can be detected. The advantage of such multicistronic embodiments is that the number of 'false positives' can be reduced by analyzing whether the protein of which the presence can be detected is expressed as well (i.e. besides sufficient selectable marker protein to allow growth of the host cells in the presence of the growth inhibitor). A protein of which the presence can be detected can be almost any protein, since for most proteins the presence can be detected for instance by antibodies, for instance in an ELISA. In preferred embodiments however, the protein of which the presence can be detected is a reporter protein as well known to the person skilled in the art, for instance a green fluorescent protein (GFP) or a derivative thereof, luciferase, beta-galactosidase, SEAP, CAT, an enzyme catalyzing a reaction that can be detected by adding substrate, and the like. These proteins can easily be detected for instance by forming a colour deposit or by fluorescence under certain well known conditions. The protein of which the presence can be detected can also be another selectable marker protein, i.e. one providing resistance to another selection agent, so that subsequent or concomitant selection with this second selection agent will detect the presence of this protein (indirectly: the protein must be present otherwise the cells would not grow), and therewith reduce the number of false positives. In such multicistronic transcription units used for screening in the method of the present invention, both configurations as disclosed in WO 2006/048459 and as disclosed in US 2006/0141577 can be used. In one embodiment therefore, the transcription unit in the screening method of the invention is a multicistronic transcription unit comprising in the following order: a) the promoter; b) the sequence encoding the selectable marker protein that protects a host cell from the lethal or growth-inhibitory effects of a selection agent; and c) the sequence encoding a protein of which the presence can be detected. As disclosed in WO 2006/048459, in this first embodiment it is strongly preferred that the selectable marker protein under b) is devoid of ATG sequences, so the first ATG will be the startcodon of the downstream protein in the cistron. In another embodiment, the transcription unit in the screening method of the invention is a multicistronic transcription unit comprising in the following order: a) the promoter; b) the sequence encoding a protein of which the presence can be detected; and c) an internal ribosome entry site (IRES), operably linked to d) the sequence encoding the selectable marker protein that provides resistance to the growth inhibitor. Multicistronic transcription units of this second embodiment have been disclosed in US 2006/0141577.

The screening method of the present invention allows for obtaining the desired expression augmenting DNA fragment from host cells that still can grow in the presence of the growth inhibitor after at least two weeks, by using routine molecular cloning methods well known to the person skilled in the art. Further rounds of screening may be performed to reduce the complexity of the library comprising the variety of fragment-comprising vectors, if desirable. Using the known sequence of the vectors, the DNA fragments with suspected expression augmenting activity resulting from a screening round can be cloned, for instance using the polymerase chain reaction (PCR), employing primers surrounding the site in the screening vector in which the variety of fragments have been cloned. The sequence of the expression augmenting DNA fragment can be analysed, and expression augmenting activity can be confirmed under a wide variety of conditions, if desired.

The host cells with the expression augmenting DNA fragments identified in the screening method of the present invention should be able to grow in the presence of the selection agent after at least one week, preferably after at least two weeks. This ensures that the selectable marker protein is stably expressed, and thus stable expression augmenting DNA fragments are isolated, while ruling out any fragments that work only very shortly. In certain embodiments, this selection step may be continued for at least 3 weeks, or even (at least) 4 weeks, 5 weeks, or more. The optimal minimum selection time may depend in part from the selection agent and the concentration thereof, but in any case host cells that survive after a certain selection period will remain resistant to the selection agent, so that in principle there is no upper limit to the selection time. In practice, the person skilled in the art will easily empirically find a suitable selection time. If for instance host cells are grown on plates containing the selection agent, one can simply wait until colonies are formed.

In preferred embodiments, the vectors are not replicating in the host cells, and will integrate (randomly) into the host cell genome. This is in contrast to for instance the assay used for obtaining STAR elements, where episomal vectors were used (WO 03/004704). One advantage of using integrating vectors is that only a limited number of copies of the vector will usually integrate into the genome, so that false-positives solely resulting from high copy numbers are avoided. In addition, recombinant expression systems in general preferably use integrated transgenes because of stability. Hence another advantage in screening according to the present invention with integrated vectors may be that the obtained expression augmenting DNA fragments then by definition function when integrated into the genome of host cells.

In one embodiment, the host cells in the screening method of the invention are CHO cells. This ensures that expression augmenting DNA fragments are obtained that are functional in a widely used host cell for recombinant expression purposes, i.e. CHO cells. Clearly, other eukaryotic, preferably mammalian, host cells can also be used according to the screening method of the invention.

In the screening method, the invention employs fragment-containing vectors, which contain a sequence encoding a selectable marker protein with a GTG or TTG startcodon, and further containing DNA fragments of between about 50 and 5000 base pairs. A collection of such vectors forms a library, which is a suitable intermediate product that can be used in the screening method of the invention. In a separate aspect the invention therefore provides a library comprising a variety of fragment-comprising vectors, said vectors comprising DNA fragments having a size of between about 50 and 5000 base pairs, said DNA fragments being located at a distance of less than about 5000 base pairs from a transcription unit, said transcription unit comprising a promoter operably linked to sequence encoding a selectable marker protein that protects a host cell from the lethal or growth-inhibitory effects of a selection agent, wherein the sequence encoding the selectable marker protein has a GTG startcodon or a TTG startcodon. It will be clear that the library can be varied along the embodiments disclosed above for the screening method. A library as used herein is a collection of vectors, comprising the same backbone vector with a single DNA fragment cloned in each backbone vector, and in said collection containing at least 5 different DNA fragments, and in certain embodiments at least 10, 100, 1000, $10^4$, $10^5$, $10^6$, $10^7$, $10^8$, $10^9$, $10^{10}$, $10^{11}$, $10^{12}$ or more different DNA fragments cloned into the backbone vectors. Higher complexity of the library has the advantage of increasing the chance of obtaining expression augmenting DNA fragments. The method allows to screen parts of or complete genomes for fragments with expression augmenting activity. After one round of screening with the screening method, it is possible to create a sub-library that is enriched for fragments with expression augmenting activity. It will be clear that such a sub-library is encompassed within the scope of the term library as used herein.

The expression augmenting DNA fragments that can be obtained by the screening method of the invention, can be used for increasing the expression level from an expression cassette on a DNA molecule. To this purpose, an expression augmenting DNA fragment obtained is cloned in an expression cassette, which is used for recombinant expression, according to principles and methods well known to the skilled person. In certain embodiments for example, the expression augmenting DNA fragment is cloned at a distance of less than 2 kb from a transcription unit comprising a promoter operably linked to sequences of which expression is desired, e.g. protein encoding sequences. The resulting expression cassette is used for recombinant expression in cells.

An 'expression cassette' as used herein is a nucleic acid sequence comprising at least a promoter functionally linked to a sequence of which expression is desired. Preferably, an expression cassette further contains transcription termination and polyadenylation sequences. Other regulatory sequences such as enhancers may also be included.

The promoter must be capable of functioning in a eukaryotic host cell, i.e. it must be capable of driving transcription of the transcription unit. The expression cassette may optionally further contain other elements known in the art, e.g. splice sites to comprise introns, and the like. In some embodiments, an intron is present behind the promoter and before the sequence encoding the selectable marker polypeptide.

To obtain expression of nucleic acid sequences encoding protein, it is well known to those skilled in the art that sequences capable of driving such expression, can be functionally linked to the nucleic acid sequences encoding the protein, resulting in recombinant nucleic acid molecules encoding a protein in expressible format. In general, the promoter sequence is placed upstream of the sequences that should be expressed. Much used expression vectors are available in the art, e.g. the pcDNA and pEF vector series of Invitrogen, pMSCV and pTK-Hyg from BD Sciences, pCMV-Script from Stratagene, etc, which can be used to obtain suitable promoters and/or transcription terminator sequences, polyA sequences, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (Das et al, 1985), and the like. Suitable promoters can also be derived from eukaryotic cells, such as methallothionein (MT) promoters, elongation factor 1α (EF-1α) promoter (Gill et al., 2001), ubiquitin C or UB6 promoter (Gill et al., 2001; Schorpp et al, 1996), actin promoter, an immunoglobulin promoter, heat shock promoters, and the like. Some preferred promoters for obtaining expression in eukaryotic cells, which are suitable promoters in the present invention, are the CMV-promoter, a mammalian EF1-alpha promoter, a mammalian ubiquitin promoter such as a ubiquitin C promoter, or a SV40 promoter (e.g. obtainable from pIRES, cat. no. 631605, BD Sciences). Testing for promoter function and strength of a promoter is a matter of routine for a person skilled in the art, and in general may for instance encompass cloning a test gene such as lacZ, luciferase, GFP, etc. behind the promoter sequence, and test for expression of the test gene. Of course, promoters may be altered by deletion, addition, mutation of sequences therein, and tested for functionality, to find new, attenuated, or improved promoter sequences. Strong promoters that give high transcription levels in the eukaryotic cells of choice are preferred. A heterologous promoter as used herein is defined as a promoter which is not the natural promoter of said sequence of interest. In other words, some form of human intervention, e.g. molecular cloning, has been used at any point in time to make the functional combination of a heterologous promoter with a nucleic acid of interest, and it is readily understood in this context that a heterologous promoter can be derived from the same or from a different organism as the sequence of interest.

An example of a suitable signal for transcription termination that can be used is the SV40 polyadenylation site (Kaufman and Sharp, 1982), or the bovine growth hormone polyadenylation signal (U.S. Pat. No. 5,122,458).

In another aspect, the present invention thus provides a recombinant DNA molecule comprising an expression augmenting DNA fragment selected from the group consisting of: a) SEQ. ID. NO. 3 (47D); b) SEQ. ID. NO. 4 (44F); c) fragments a) or b), wherein said fragment is at least 50 bp in length and has expression augmenting activity; and d) sequences that are at least 70% identical in nucleotide sequence to a), b) or c), wherein said sequences have expression augmenting activity; said recombinant DNA molecule further comprising an expression cassette, said expression cassette comprising a heterologous promoter linked to a nucleic acid of interest.

Sequences 47D and 44F where retrieved from the human genome using screens of the present invention, and where subsequently confirmed to have expression augmenting activity. It is clear to the person skilled in the art that these fragments could be used as a starting point for preparing and testing fragments or derivatives thereof, e.g. by deletions, additions, substitutions of bases, combinations thereof and the like, and hence such fragments or derivatives are also encompassed within the present invention. A sequence has expression augmenting activity as used herein when such a sequence provides on average at least 10% higher expression as compared to the identical situation but without said sequence being present. In preferred embodiments, an expression augmenting DNA fragment confers at least 20%, preferably at least 30%, more preferably at least 50%, still more preferably at least 100%, or even more, higher expression as compared to the situation where said fragment is not present. This can be tested according to routine methods available to the skilled person. For instance, this can be suitably tested in an expression construct as used for the screening method disclosed herein: a CMV promoter operably linked to a bicistronic transcription unit comprising a TTG Zeo coding sequence (encoding zeocin resistance and having a TTG startcodon) followed by a green fluorescent protein (d2EGFP) encoding sequence and a transcription termination sequence (see e.g. example 1 below). A fragment has expression augmenting activity when, if positioned upstream of the CMV promoter in such a construct, the mean fluorescence in zeocin resistant colonies is at least 10% higher as compared to the control situation without such fragment under otherwise identical conditions. The sequences 47D and 44F have a size of less than 1 kb, which is advantageous in that they do not require so much space in an expression vector, and hence more capacity remains therein for other sequences of interest. Nevertheless, even smaller fragments of these fragments (e.g. fragments of between about 50-750 bp, 100-700, 200-700, 300-700, 400-700, 500-700 bp, etc, e.g. fragments of about 50, 100, 150, 200, 250, 300, 350, 400, 450, 500, 550, 600, 650, 700 bp) may already confer expression augmenting activity. It is also possible to lengthen these elements by adding back sequences from the genome, e.g. to a total of about 1 kb, 1.5 kb, 2 kb, and testing the resulting fragments for expression augmenting activity, which possibly could be higher, but also equal to, or lower, than the activity of the disclosed elements. It is likely that variation will be possible in the expression augmenting DNA fragments, resulting in derivative fragments that still have expression augmenting activity. Such smaller fragments and/or derivative fragments can be routinely prepared and tested, and altered fragments with decreased, similar, or increased activity could be obtained. Preferably, said sequences are at least 80% identical, more preferably at least 90% identical and still more preferably at least 95% identical to the reference native sequence or functional fragment thereof. For fragments of a given sequence, percent identity refers to that portion of the reference native sequence that is found in the fragment. It may also be possible to find homologous fragments to fragments 47D or 44F, from genomes of other organisms, e.g. mammalian organisms, e.g. monkey, rat, mouse, hamster, etc. Such orthologous or paralogous fragments and derivatives thereof are also encompassed in the present invention, when they are at least 70% identical to a sequence as disclosed herein and when they have expression augmenting activity as defined herein.

An expression cassette of the invention may contain a monocistronic or a multicistronic transcription unit. It contains a promoter and a sequence of which expression is desired and usually a transcription termination signal. In one embodiment, an expression cassette of the invention contains a monocistronic transcription unit comprising the nucleic acid of interest. In other embodiments, the nucleic acid of interest is present in a multicistronic transcription unit that further encodes a selectable marker protein. In certain embodiments thereof, the multicistronic transcription unit in the coding strand for the selectable marker protein comprises a translation start sequence for the selectable marker protein chosen from the group consisting of: a) an ATG startcodon in a non-optimal context for translation initiation, comprising the sequence (C/T)(A/T/G)(A/T/G)ATG(A/T/C) wherein the startcodon is underlined; b) a GTG startcodon; c) a TTG startcodon; d) a CTG startcodon; e) a ATT startcodon; and f) a ACG startcodon. In such embodiments, the sequence encoding the selectable marker protein may be positioned either i) upstream of the nucleic acid of interest, or ii) downstream of the nucleic acid of interest. In situation i), the sequence encoding the selectable marker protein preferably is devoid of internal ATGs (and is in effect therefore as a whole devoid of any ATGs, since the startcodon is a GTG or a TTG), so that the nucleic acid of interest is expressed (see WO 2006/048459 for this concept, and for methods and examples of creating DNA encoding functional selectable marker proteins devoid of ATG sequences). In situation ii) the nucleic acid of interest is upstream and is preferably followed by an internal ribosome entry site (IRES), which is operably linked to the sequence encoding the selectable marker protein (having the GTG or TTG startcodon), so that the selectable marker protein is translated from the IRES (see US 2006/0141577 for this concept).

As used herein, an "internal ribosome entry site" or "IRES" refers to an element that promotes direct internal ribosome entry to the initiation codon, such as normally an ATG, but in this invention preferably GTG or TTG, of a cistron (a protein encoding region), thereby leading to the cap-independent translation of the gene. IRES sequences and use thereof for expression are well known to the person skilled in the art, as taught in US 2006/0141577 and PCT/EP2007/051696, incorporated by reference herein. See also, e.g., Jackson R J, Howell M T, Kaminski A (1990) Trends Biochem Sci 15 (12): 477-83), Jackson R J and Kaminski, A. (1995) RNA 1 (10): 985-1000, Martinez-Salas, 1999, Venkatesan & Dasgupta, 2001, Rees et al, 1996, and Mizuguchi et al., 2000.

In certain embodiments, the nucleic acid of interest encodes all or part of a polypeptide of interest.

In certain embodiments, the expression augmenting DNA fragments are situated upstream of the promoter in the expression cassette.

In certain embodiments, the expression augmenting DNA fragments are separated by less than 5 kb, preferably less than 2 kb, more preferably less than 1 kb from the promoter when located upstream thereof, or from the transcription termination signal of the expression cassette when located downstream thereof. In preferred embodiments, the expression augmenting DNA fragments are upstream of the promoter and separated by less than 800, 700, 600, preferably by less than about 500, 400, 300, 200, 100 or 50 base pairs from the (5' end of the) promoter sequence in the expression cassette.

It is not known whether the obtained expression augmenting sequences would also qualify as STAR sequences using the assay as described in WO 2006/048459. In any case, since they have been obtained by a fundamentally different method, they may be combined with other elements that influence expression, such as chromatin control elements as discussed in WO 2006/048459, and then tested for activity which could with respect to expression levels in certain cases be additive or even synergistic with at least some of those chromatin control elements. Therefore, in certain embodiments, the DNA molecules provided by the present invention besides an expression augmenting DNA fragment according to the invention further comprise a chromatin control element, such as a MAR, or a STAR element (see WO 2006/048459 for examples of such elements and use thereof). Even if they would not be additive or synergistic, the expression augmenting DNA fragments of the present invention may replace some of the chromatin control elements and be used as an alternative thereto, with the advantage of having a smaller size.

In certain embodiments, a DNA molecule according to the invention is part of a vector, e.g. a plasmid. Such vectors can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art. In preferred embodiments, the present invention also uses these types of DNA molecules to deliver its improved transgene expression system. A preferred embodiment of the invention is the use of plasmid DNA for delivery of the expression system.

The vector used can be any vector that is suitable for cloning DNA and that can be used for transcription of a nucleic acid of interest. When host cells are used it is preferred that the vector is an integrating vector. Alternatively, the vector may be an episomally replicating vector.

A nucleic acid of interest in preferred embodiments encodes a polypeptide of interest. A polypeptide of interest according to the invention can be any protein, and may be a monomeric protein or a (part of a) multimeric protein. A multimeric protein comprises at least two polypeptide chains. Non-limiting examples of a protein of interest according to the invention are enzymes, hormones, immunoglobulin chains, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

In certain embodiments, an expression cassette of the invention encodes an immunoglobulin heavy or light chain or an antigen binding part, derivative and/or analogue thereof. In one embodiment a protein expression unit according to the invention is provided, wherein said protein of interest is an immunoglobulin heavy chain. In another embodiment a protein expression unit according to the invention is provided, wherein said protein of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. Preferably, such an antibody is a human or humanized antibody. In certain embodiments thereof, it is an IgG, IgA, or IgM antibody. An immunoglobulin may be encoded by the heavy and light chains on different expression cassettes, or on a single expression cassette.

The polypeptide of interest may be from any source, and in certain embodiments is a mammalian protein, an artificial protein (e.g. a fusion protein or mutated protein), and preferably is a human protein.

Obviously, the configurations of the expression cassettes of the invention may also be used when the ultimate goal is not the production of a polypeptide of interest, but the RNA itself, for instance for producing increased quantities of RNA from an expression cassette, which may be used for purposes of regulating other genes (e.g. RNAi, antisense RNA), gene therapy, in vitro protein production, etc.

The invention further provides cells comprising a recombinant DNA molecule according to the present invention. In certain embodiments, said cell is a mammalian cell, such as a human cell, a hamster cell, a mouse cell, and the like. In certain embodiments, said cell is a CHO cell.

DNA molecules comprising multicistronic transcription units and/or expression cassettes according to the invention can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability, to express heterologous or homologous proteins.

Prokaryotic host cells can be used to propagate and/or perform genetic engineering with the DNA molecules of the invention, especially when present on plasmids capable of replicating in prokaryotic host cells such as bacteria.

A host cell according to the present invention preferably is a eukaryotic cell, more preferably a mammalian cell, such as a rodent cell or a human cell or fusion between different cells. In certain non-limiting embodiments, said host cell is a U-2 OS osteosarcoma, CHO (Chinese hamster ovary), HEK 293, HuNS-1 myeloma, WERI-Rb-1 retinoblastoma, BHK, COS, Vero, non-secreting mouse myeloma Sp2/0-Ag 14, non-secreting mouse myeloma NS0, NCI-H295R adrenal gland carcinomal or a PER.C6® cell. PER.C6 cells for the purpose of the present invention means cells from an upstream or downstream passage or a descendent of an upstream or downstream passage of cells as deposited under ECACC no. 96022940 (U.S. Pat. No. 5,994,128), i.e. having the characteristics of those cells. It has been previously shown that such cells are capable of expression of proteins at high levels (e.g. WO 00/63403, and Jones et al, 2003). In certain preferred embodiments, the host cells are CHO cells, for instance CHO-K1, CHO-S, CHO-DG44, CHO-DUKXB11, and the like. In certain embodiments, said CHO cells have a dhfr$^-$ phenotype.

Such eukaryotic host cells can express desired polypeptides, and are often used for that purpose. They can be obtained by introduction of a DNA molecule of the invention, preferably in the form of an expression cassette, into the cells. Preferably, the expression cassette is integrated in the genome of the host cells, which can be in different positions in various host cells, and selection will provide for a clone where the transgene is integrated in a suitable position, leading to a host cell clone with desired properties in terms of expression levels, stability, growth characteristics, and the like. Alternatively the transcription unit may be targeted or randomly selected for integration into a chromosomal region that is transcriptionally active, e.g. behind a promoter present in the genome.

Preferably the host cells are from a stable clone that can be selected and propagated according to standard procedures known to the person skilled in the art. A culture of such a clone is capable of producing polypeptide of interest, if the cells comprise the transcription unit encoding such. Cells according to the invention preferably are able to grow in suspension culture in serum-free medium.

In preferred embodiments, the DNA molecule of the invention is integrated into the genome of the eukaryotic host cell according to the invention. This will provide for stable inheritance of the DNA molecule.

The invention further provides a method for producing a polypeptide of interest, comprising culturing a cell comprising a recombinant DNA molecule according to the invention, to express the nucleic acid encoding the protein of interest in said cell. In preferred embodiments, the protein of interest is harvested from said cell or from the culture medium or from both. In preferred embodiments, said cell is a mammalian cell, for instance a CHO cell. In preferred embodiments of this method, the recombinant DNA molecule of the invention is integrated into the genome of the cell. In certain embodiments, the nucleic acid encoding the protein of interest is present in a multicistronic transcription unit. In certain embodiments thereof, such a multicistronic transcription unit is one according to the disclosure of WO 2006/048459 or US 2006/0141577.

Introduction of nucleic acid that is to be expressed in a cell, can be done by one of several methods, which as such are known to the person skilled in the art, also dependent on the format of the nucleic acid to be introduced. Said methods include but are not limited to transfection, infection, injection, transformation, and the like.

In certain embodiments, selection agent is present in the culture medium at least part of the time during the culturing, either in sufficient concentrations to select for cells expressing the selectable marker polypeptide or in lower concentrations. In preferred embodiments, selection agent is no longer present in the culture medium during the production phase when the polypeptide is expressed.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

The conditions for growing or multiplying cells (see e.g. Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In a preferred embodiment, the expressed protein is collected (isolated), either from the cells or from the culture medium or from both. It may then be further purified using known methods, e.g. filtration, column chromatography, etc, by methods generally known to the person skilled in the art.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, 2$^{nd}$ edition, 1989; Current Protocols in Molecular Biology, Ausubel F M, et al, eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further explained in the following example. The example does not limit the invention in any way. It merely serves to clarify the invention.

EXAMPLE

Example 1 describes the screen for expression augmenting DNA fragments of the present invention, and it will be clear that the variations described in examples 1-19 of WO 2006/048459 can be applied and tested for the screen for expression augmenting DNA fragments, and that the expression augmenting DNA fragments obtained could be incorporated in expression cassettes, included those containing multicistronic transcription units of WO 2006/048459 and of US 2006/0141577.

Example 1

Use of the STAR-Select System to Identify Expression Augmenting DNA Fragments

The selection system of WO 2006/048459 wherein a GTG or TTG startcodon is used for the selectable marker protein mRNA is very stringent. Application of the selection system results in almost no colonies, unless STAR elements are incorporated in the construct to enhance the CMV promoter (see WO 2006/048459). This system can in principle be used for a systematic screen to find genomic DNA fragments, potentially other than STAR elements, that enhance the CMV promoter in such a manner that colonies easily survive under a given selection pressure. Here we describe a systematic search for such expression augmenting DNA fragments.

Results

Approximately 10 μg human genomic DNA (Promega, G147A 16040303) was cut with the restriction enzyme Sau3AI for 10 minutes at 37° C. to obtain random fragments between 200 and 1000 bp. The digested DNA was run on a 1.2% agarose gel and the smear containing fragments between 200 and 1000 bp was excised and the DNA was purified and isolated. This pool of DNA fragments was cloned in the BglII restriction site upstream of the CMV promoter, which was followed by the TTG Zeo and d2EGFP cassettes. The ligation mix was transformed to E. coli XL10 Gold (Stratagene). Approximately 20,000 colonies were pooled, grown in liquid broth medium and DNA was isolated using a Qiagen maxiprep column. Approximately 300 μg DNA was isolated. Per approximately 700,000 CHO-K1 cells in a well of a 6-wells plate, 3 μg DNA was transfected using Lipofectamine 2000 (Invitrogen). This procedure was performed for 36 wells. As control, 12 wells were transfected with a construct, containing the CMV promoter, TTG Zeo and d2EGFP, but no inserted genomic DNA. Both cells that were transfected with control plasmids and cells that were transfected with the library were grown in the presence of 100 μg/ml Zeocin in HAM-F12 medium (Invitrogen)+10% FBS (Invitrogen). Cells were allowed to grow for three weeks, in which time some colonies formed. Out of the 12 wells transfected control plasmid, approximately 5 colonies formed. However, inspection under a fluorescence microscope revealed that these colonies were not green, implicating that they produced only little d2EGFP. In contrast, 72 colonies formed as result of the transfections with the library. All 72 colonies were isolated and propagated, before measuring d2EGFP expression levels using a flowcytometer (Beckman Coulter). Of the highest expressing 25 CHO colonies, genomic DNA was isolated and analyzed by PCR, for the presence of library fragments. For the PCR the following primers were used, that recognized the flanking sequences of the cloning sites.

```
                                             (SEQ. ID. NO. 1)
Primer A: gatcggcgcgcccgaaagggcccgtaccttaattaaag (SEQ. ID. NO. 2)
Primer B: aggcggcgcgcccgcgaaattaggcaaaggaattatcag.
```

Per original CHO clone PCR product of various lengths were observed, indicating that multiple DNA fragments from the library had integrated in such original CHO clone. To identify potential expression augmenting DNA fragments, the PCR products were cloned into the AscI site of the TTG Zeo d2EGFP vector. The ligation mix was transformed to E. coli and up to 10 different bacterial colonies were analyzed for inserts. When more than five DNA inserts with different sizes were found per original CHO clone, the analysis was not pursued. Six original CHO clones harboured less than five DNA inserts, indicating a limited complexity. From these six original CHO clones, in total 16 constructs were recovered that contained DNA fragments, upstream from TTG Zeo. These 16 constructs were re-transfected to CHO-K1. Transfection of one construct (construct 47D; SEQ. ID. NO. 3) resulted in the generation of more than 25 clones per transfection that showed high levels of d2EGFP expression under a fluorescence microscope. Transfection of a second construct (44F; SEQ. ID. NO. 4) resulted in the generation of 7 clones that showed higher d2EGFP expression under a fluorescence microscope. The other 14 constructs either gave very low d2EGFP expression levels as monitored under a fluorescence microscope, and were not pursued further.

Analysis of the 7 picked clones that were transfected with construct 44F, showed that d2EGFP expression levels were significantly elevated, when compared to the control colonies (FIG. 1). Also analysis of 12 randomly picked clones that were transfected with construct 47D, showed that d2EGFP expression levels were significantly elevated, when compared to the control colonies (FIG. 1). As positive control we compared a TTG Zeo d2EFGP construct, flanked with STAR elements 7 and 67 upstream and STAR 7 downstream. As compared with the STAR 7/67/7 the 47D element induced comparable, though slightly less high d2EGFP values. Since construct 47D induced highest d2EGFP values (FIG. 1), we continued analysis of this construct in the context of another CHO cell line, CHO-DG44.

Figure 2:
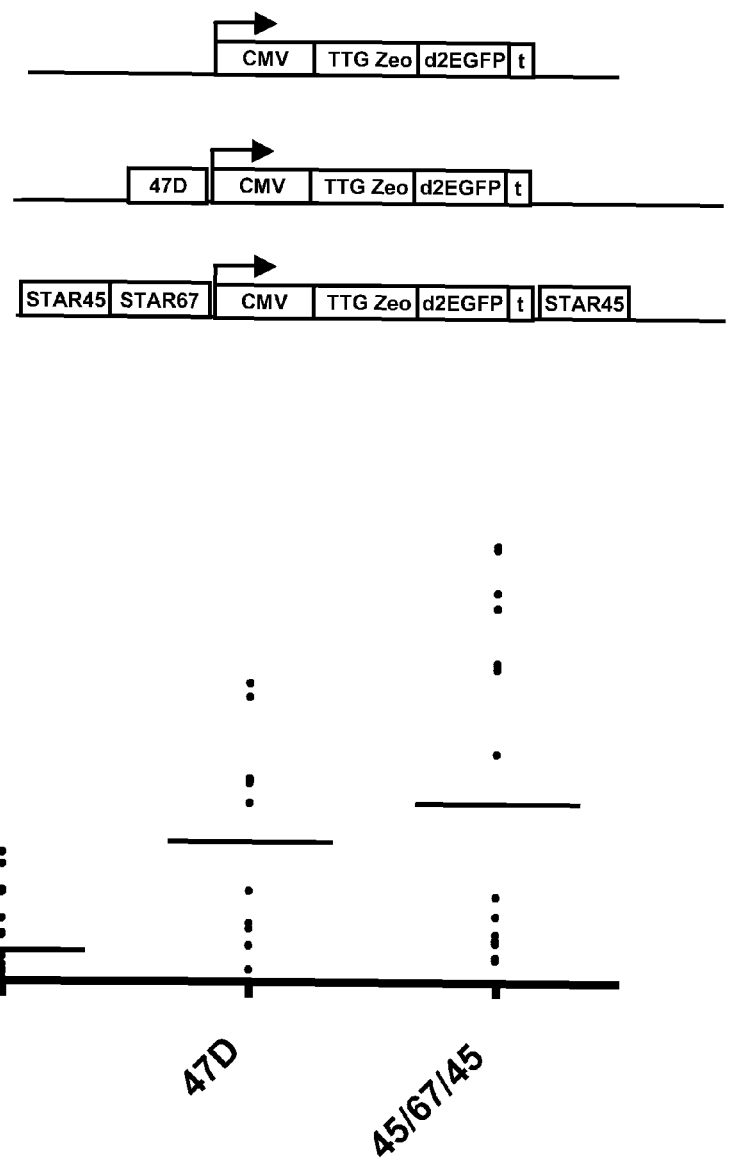
FIG. 2. As FIG. 1, but in CHO-DG44 cells. Expression augmenting DNA fragment 47D was used. See example 1 for details.

The construct containing the 47D element was also transfected to CHO-DG44 cells. The construct was transfected using Lipofectamine 2000 (Invitrogen). Cells were grown in the presence of 100 µg/ml Zeocin in HAM-F12 medium (Invitrogen)+10% FBS (Invitrogen) and DMEM (1:1). Cells were allowed to grow for three weeks, in which time colonies formed. Analysis of 18 randomly picked clones that were transfected with construct 47D, showed that d2EGFP expression levels were significantly elevated, when compared to the control CHO-DG44 transfected colonies (FIG. 2). As positive control we compared a TTG Zeo d2EFGP construct, flanked with STAR elements 45 and 67 upstream and STAR 45 downstream. As compared with the STAR 45/67/45 the novel 47D element induced comparable, though slightly less high d2EGFP values.

These results show that it is possible to isolate expression augmenting DNA elements by employing the stringent TTG Zeo selection marker as screening methodology. The skilled person will understand that the vectors used for screening, and in particular the DNA encoding the selectable marker protein, can be varied along the lines discussed in the examples of WO 2006/048459.

REFERENCES

Chung J H, Whiteley M, and Felsenfeld G. (1993) A 5' element of the chicken beta-globin domain serves as an insulator in human erythroid cells and protects against position effect in *Drosophila*. Cell 74: 505-514.

Chung J H, Bell A C, Felsenfeld G. (1997). Characterization of the chicken beta-globin insulator. *Proc Natl Acad Sci USA* 94: 575-580.

Das, G C, Niyogi, S K, and Salzman, N P. (1985) SV40 promoters and their regulation *Prog Nucleic Acid Res Mol Biol* 32, 217-236.

Gill D R, Smyth S E, Goddard C A, Pringle I A, Higgins C F, Colledge W H, and Hyde S C. (2001) Increased persistence of lung gene expression using plasmids containing the ubiquitin C or elongation factor 1α promoter. Gene Therapy 8: 1539-1546.

Jones D, Kroos N, Anema R, Van Montfort B, Vooys A, Van Der Kraats S, Van Der Helm E, Smits S, Schouten J, Brouwer K, Lagerwerf F, Van Berkel P, Opstelten D-J, Logtenberg T, Bout A (2003) High-level expression of recombinant IgG in the human cell line PER.C6. Biotechnol. Prog. 19: 163-168.

Kaufman, R J. (2000) Overview of vector design for mammalian gene expression *Mol Biotechnol* 16, 151-160.

Kaufman, R J, and Sharp, P A. (1982) Construction of a modular dihydrofolate reductase cDNA gene: analysis of signals utilized for efficient expression *Mol Cell Biol* 2, 1304-1319.

Kellum R, and Schedl P. (1991) A position-effect assay for boundaries of higher order chromosomal domains. Cell 64: 941-950.

Kozak M. (1986) Point mutations define a sequence flanking the AUG initiator codon that modulates translation by eukaryotic ribosomes. Cell 44: 283-292.

Kozak M. (1987) An analysis of 5'-noncoding sequences from 699 vertebrate messenger RNAs. Nucleic Acids Res. 15: 8125-8148.

Kozak M. (1989) Context effects and inefficient initiation at non-AUG codons in eucaryotic cell-free translation systems. Mol Cell Biol. 9: 5073-5080.

Kozak M. (1990) Downstream secondary structure facilitates recognition of initiator codons by eukaryotic ribosomes. Proc Natl Acad Sci USA 87:8301-8305.

Kozak M. (1997) Recognition of AUG and alternative initiator codons is augmented by G in position +4 but is not generally affected by the nucleotides in positions +5 and +6. EMBO J. 16: 2482-2492.

Kozak M. (2002) Pushing the limits of the scanning mechanism for initiation of translation. Gene 299: 1-34.

Kwaks T H, Barnett P, Hemrika W, Siersma T, Sewalt R G, Satijn D P, Brons J F, van Blokland R, Kwakman P, Kruckeberg A L, Kelder A, Otte A P. (2003) Identification of anti-repressor elements that confer high and stable protein production in mammalian cells. *Nat Biotechnol* 21, 553-558. Erratum in: Nat Biotechnol 21, 822 (2003).

Phi-Van L, Von Kreis J P, Ostertag W, and Strätling W H. (1990) The chicken lysozyme 5' matrix attachment region increases transcription from a heterologous promoter in heterologous cells and dampens position effects on the expression of transfected genes. Mol. Cell. Biol. 10: 2302-2307.

Martinez-Salas, E. (1999) Internal ribosome entry site biology and its use in expression vectors *Curr Opin Biotechnol* 10, 458-64.

Mizuguchi, H, Xu, Z, Ishii-Watabe, A, Uchida, E, and Hayakawa, T. (2000) IRES-dependent second gene expression is significantly lower than cap-dependent first gene expression in a bicistronic vector *Mol Ther* 1, 376-82.

Rees, S, Coote, J, Stables, J, Goodson, S, Harris, S, and Lee, M G. (1996) Bicistronic vector for the creation of stable mammalian cell lines that predisposes all antibiotic-resistant cells to express recombinant protein *Biotechniques* 20, 102-104, 106, 108-110.

Schorpp, M, Jager, R, Schellander, K, Schenkel, J, Wagner, E F, Weiher, H, and Angel, P. (1996) The human ubiquitin C promoter directs high ubiquitous expression of transgenes in mice *Nucleic Acids Res* 24, 1787-8.

Venkatesan, A, and Dasgupta, A. (2001) Novel fluorescence-based screen to identify small synthetic internal ribosome entry site elements *Mol Cell Biol* 21, 2826-37.

West A G, Gaszner M, Felsenfeld G (2002) Insulators: many functions, many mechanisms. Genes Dev. 16: 271-288.

The invention claimed is:

1. A recombinant DNA molecule comprising an expression augmenting DNA fragment comprising SEQ ID NO: 3, said recombinant DNA molecule further comprising an expression cassette, said expression cassette comprising a heterologous promoter linked to a nucleic acid of interest, and wherein the expression augmenting DNA fragment is situated upstream of the promoter in the expression cassette.

2. The recombinant DNA molecule according to claim 1, wherein said nucleic acid of interest encodes all or part of a protein of interest.

3. The recombinant DNA molecule according to claim 1, wherein said expression augmenting DNA fragment and said promoter are separated by less than 2 kb.

4. The recombinant DNA molecule according to claim 1, wherein said nucleic acid of interest is present in a multicistronic transcription unit that further encodes a selectable marker protein.

5. The recombinant DNA molecule according to claim 4, wherein the transcription unit that encodes the selectable marker protein in the coding strand comprises a translation start sequence for the selectable marker protein chosen from the group consisting of: a) an ATG start codon in a non-optimal context for translation initiation, comprising the sequence (C/T)(A/T/G)(A/T/G)ATG(A/T/C) wherein the start codon is underlined; b) a GTG start codon; c) a TTG start codon; d) a CTG start codon; e) an ATT start codon; and f) an ACG start codon.

6. An isolated cell comprising the recombinant DNA molecule of claim 1.

7. The cell according to claim 6, which is a mammalian cell.

8. The cell according to claim 7, which is a CHO cell.

* * * * *